(12) United States Patent
Sakai et al.

(10) Patent No.: US 7,612,141 B2
(45) Date of Patent: Nov. 3, 2009

(54) HAIR CLEANSING COMPOSITION

(75) Inventors: Hirokazu Sakai, Tokyo (JP); Hiroto Tanamachi, Tokyo (JP); Yoshimasa Okamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 347 days.

(21) Appl. No.: 11/245,071

(22) Filed: Oct. 7, 2005

(65) Prior Publication Data

US 2006/0036046 A1 Feb. 16, 2006

Related U.S. Application Data

(63) Continuation of application No. 10/743,833, filed on Dec. 24, 2003, now abandoned.

(30) Foreign Application Priority Data

Dec. 25, 2002 (JP) ............................. 2002-375320

(51) Int. Cl.
C08L 83/00 (2006.01)
(52) U.S. Cl. ...................... 524/588; 514/613
(58) Field of Classification Search ............... 524/588; 514/613
See application file for complete search history.

(56) References Cited

U.S. PATENT DOCUMENTS

| | | |
|---|---|---|
| 5,476,671 A | 12/1995 | Cho et al. |
| 5,525,709 A | 6/1996 | Davey et al. |
| 5,618,523 A | 4/1997 | Zysman et al. |
| 5,656,668 A | 8/1997 | Motion et al. |
| 5,661,118 A | 8/1997 | Cauwet et al. |
| 5,665,778 A | 9/1997 | Semeria et al. |
| 5,869,711 A | 2/1999 | Philippe et al. |
| 6,210,691 B1 | 4/2001 | Mahieu et al. |
| 6,685,953 B1 | 2/2004 | Hoshino et al. |

FOREIGN PATENT DOCUMENTS

| | | |
|---|---|---|
| EP | 227 994 | 7/1987 |
| EP | 646 572 | 4/1995 |
| EP | 647 617 | 4/1995 |
| EP | 0 739 625 | 10/1996 |
| EP | 736 522 | 10/1996 |
| EP | 1 166 766 | 1/2002 |
| FR | 2 673 179 | 8/1992 |
| FR | 2 819 405 | 7/2002 |
| JP | 08-502058 | 3/1996 |
| WO | 94/07844 | 4/1994 |
| WO | 94/24097 | 10/1994 |
| WO | 95/16665 | 6/1995 |
| WO | WO 00/44345 | 8/2000 |
| WO | WO 02/055053 A2 | 7/2002 |

OTHER PUBLICATIONS

"Kosmetikjahrbuch 2002", Verlag Für Chemische Industrie, XP-002295513, 2002, pp. 420-421.
K. De Polo, "A Short Textbook of Cosmetology", Verlag Für Chemische Industrie, XP-002295514, 1998, pp. 65-69.
Hardmann, Silicones, Reprinted from Encyclopedia of Polymer Science and Engineering, vol. 15, $2^{nd}$ Ed., p. 234.
Fragrance Journal, Jun. 2000, pp. 61-64 (with English Abstract).
Masato Suzuki, "Efficacy, effect and action of new cosmetic material, first press, CMC Corporation", Aug. 31, 1998, 13 pages (with full English translation).

*Primary Examiner*—Kuo-Liang Peng
(74) *Attorney, Agent, or Firm*—Oblon, Spivak, McClelland, Maier & Neustadt, L.L.P.

(57) ABSTRACT

Provided is a hair cleansing composition comprising (A) an amphipathic amide lipid, (B) an anionic surfactant and (C) a silicone. The hair cleansing composition of the present invention has advantages such as protecting hair from physical or chemical stimulation and preventing split ends or hair breakage without impairing its cleansing ability and feeling upon use, and moreover, gives to hair after shampooing a pleasant feeling to the touch and moisture retention properties such as natural smoothness, moist feeling, and suppleness which healthy hair inherently possesses, and has excellent stability.

11 Claims, No Drawings

HAIR CLEANSING COMPOSITION

FIELD OF THE INVENTION

The present invention relates to hair cleansing compositions containing an amphipathic amide lipid.

BACKGROUND OF THE INVNETION

Since hair is always daily exposed to physical stimulation by daily hair care routines such as heat drying with a hair dryer and brushing, and chemical stimulation by shampooing, permanent weaving, dyeing and bleaching, it is in a damaged state with a partial loss of component or structure. A change in hair quality due to ageing accelerates this damage and also causes the loss of suppleness which healthy hair inherently possesses.

It is a common practice to protect or repair hair in a damaged state by making up for the lost component or structure or analogue thereof. Interaction (affinity) between a protecting base and hair is considered to be important for developing a protecting or restoring function, and thus a method of using sphingolipid or protein derivative as a protecting base has been employed widely as a useful technique. For example, proposed is a hair cleansing composition containing a surfactant composed of an anionic surfactant and a bipolar ionic surfactant, a cationic polymer, and a ceramide or glycoceramide (Japanese Patent Application Laid-Open No. 59443/1996). The composition however cannot contain a sufficient amount of a protecting base such as a ceramide or glycoceramide because it has a high melting point and is liable to crystallize. Even by such a composition, sufficient hair protecting or repairing effects cannot be attained yet.

SUMMARY OF THE INVENTION

According to the present invention, there is thus provided a hair cleansing composition containing the following components (A) to (C):
(A): an amphipathic amide lipid,
(B): an anionic surfactant, and
(C): a silicone.

DETAILED DESCRIPTION OF THE INVENTION

The present invention relates to a hair cleansing composition which has, for example, excellent effects for preventing or repairing damaged hair.

The present inventors have found that a hair cleansing composition incorporated with both an amphipathic amide lipid and a silicone as a protecting base can protect hair from physical and chemical stimulation and thereby preventing spilt ends and breakage of hair, and in addition, can significantly impart hair with a pleasant feeling to the touch such as natural smoothness, moist feeling, and suppleness which healthy hair inherently possesses.

The amphipathic amide lipid as Component (A) preferably has 1 or 2 amide groups; preferably has, as a carbon chain bonded to the carbonyl group of the amide group, a $C_{5-60}$ alkyl or alkylene group which may be substituted with a hydroxy group and may contain an ester bond in its main chain; and preferably contains 1 to 5 hydroxy or $C_{1-30}$ alkoxy groups in total. The following compounds (1) to (4) are specific preferred examples of the amphipathic amide lipid.

(1) Diamide compounds represented by formula (1):

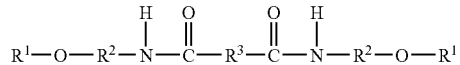

(1)

wherein, $R^1$ represents a linear or branched $C_{1-12}$ hydrocarbon group which may be substituted with a hydroxy group(s) and/or alkoxy group(s), $R^2$ represents a linear or branched divalent $C_{1-5}$ hydrocarbon group and $R^3$ represents a linear or branched divalent $C_{1-22}$ hydrocarbon group.

As $R^1$ in formula (1), linear or branched $C_{1-12}$ alkyl groups which may be substituted with 1 to 3 groups selected from the group consisting of a hydroxy group and $C_{1-6}$ alkoxy groups are preferred. Of these, unsubstituted $C_{1-12}$ alkyl groups and $C_{2-12}$ alkyl groups substituted with 1 to 2 hydroxy groups and one $C_{1-6}$ alkoxy group or with one hydroxy group and one $C_{1-6}$ alkoxy group are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl and 9-methoxynonyl groups, of which 2-hydroxyethyl, methyl, dodecyl and 2-methoxyethyl groups are preferred. Combinations of the above materials may also be used.

As $R^2$ in formula (1), linear or branched $C_{2-5}$ alkylene groups are preferred, and linear or branched $C_{2-3}$ alkylene groups are preferred. Specific examples include ethylene, trimethylene, tetramethylene, pentamethylene, 1-methylethylene, 2-methylethylene, 1-methyltrimethylene, 2-methyltrimethylene, 1,1-dimethylethylene and 2-ethyltrimethylene groups. Of these, ethylene and trimethylene groups are preferred.

As $R^3$ in formula (1), linear or branched divalent $C_{2-22}$ hydrocarbon groups are preferred, and linear or branched $C_{11-22}$ alkylene groups and alkenylene groups having 1 to 4 double bonds are more preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene and 8,11-dimethyl-7,11-octadecadienylene groups. Of these, 7,12-dimethyloctadecamethylene, 7,12-dimethyl-7,11-octadecadienylene, octadecamethylene, undecamethylene and tridecamethylene groups are preferred.

Preferred diamide compounds (1) are compounds having the above-described preferred groups as $R^1$, $R^2$ and $R^3$, respectively. Specific examples are the following compounds:

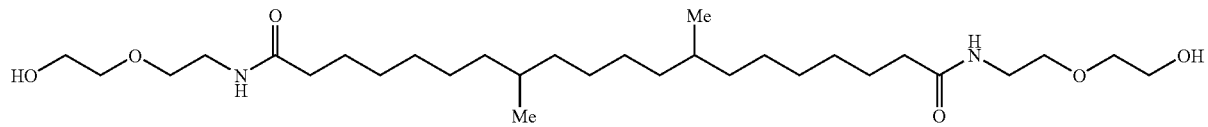

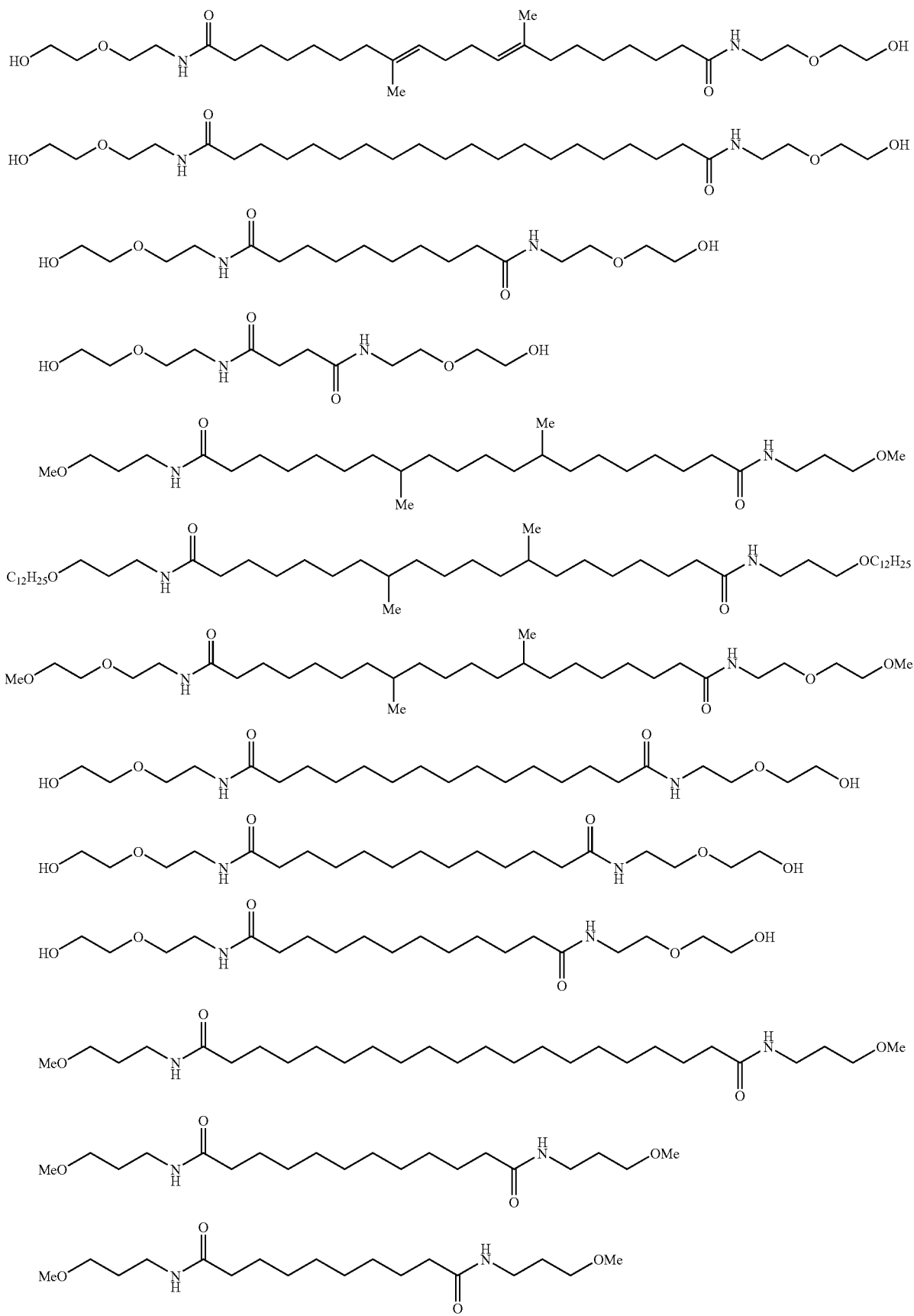

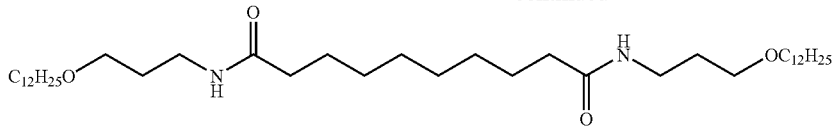

(2) Ceramides represented by the following formula (2):

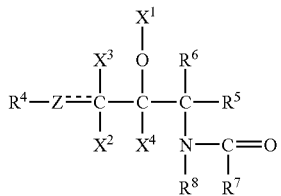

(2a) Natural ceramides or natural type ceramides represented by formula (2a), and derivatives thereof (which will hereinafter be called "natural type ceramides")

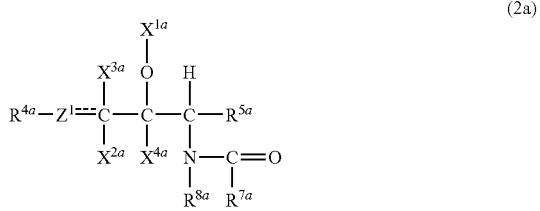

wherein, $R^4$ represents a linear, branched or cyclic, saturated or unsaturated $C_{4-30}$ hydrocarbon group which may be substituted with hydroxy, oxo or amino group(s), Z represents a methylene group, a methine group or an oxygen atom, a broken line represents the presence or absence of a π bond, $X^1$ represents a hydrogen atom, an acetyl group or a glyceryl group, or, together with the adjacent oxygen atom, forms an oxo group, $X^2$, $X^3$ and $X^4$ each independently represents a hydrogen atom, a hydroxy group or an acetoxy group (with the proviso that when Z represents a methine group, one of $X^2$ and $X^3$ represents a hydrogen atom and the other does not exist, and when —O—$X^1$ represents an oxo group, $X^4$ does not exist), $R^5$ and $R^6$ each independently represents a hydrogen atom, a hydroxy group, a hydroxymethyl group or an acetoxymethyl group, $R^7$ represents a linear, branched or cyclic, saturated $C_{5-35}$ hydrocarbon group which may be substituted with a hydroxy or amino group, or the saturated $C_{5-35}$ hydrocarbon group in which a linear, branched or cyclic, saturated or unsaturated $C_{8-22}$ fatty acid which may be substituted with hydroxy group(s) is ester-bonded at the ω-position of the hydrocarbon group, and $R^8$ represents a hydrogen atom or a linear or branched, saturated or unsaturated hydrocarbon group which may have substituent(s) selected from a hydroxy group, hydroxyalkoxy groups, alkoxy groups and an acetoxy group, and has 1 to 8 carbon atoms in total.

As $R^4$ in formula (2), linear, branched or cyclic, saturated or unsaturated $C_{7-22}$ hydrocarbon groups which may be substituted with hydroxy group(s) are preferred. As $X^1$, a hydrogen atom and a glyceryl group are preferred. It is preferred that none or one of $X^2$, $X^3$, and $X^4$ represents a hydroxy group and the others represent a hydrogen atom. It is preferred that one of $R^5$ and $R^6$ represents a hydrogen atom or a hydroxymethyl group and the other represents a hydrogen atom. In $R^7$, preferred examples of the fatty acid which may be ester-bonded or amide-bonded to the saturated hydrocarbon group at the ω-position thereof include isostearic acid, 12-hydroxystearic acid and linoleic acid. As $R^8$, a hydrogen atom and hydrocarbon groups which may be substituted with 1 to 3 substituents selected from a hydroxy group, hydroxyalkoxy groups and alkoxy groups and have 1 to 8 carbon atoms in total are preferred.

As ceramide (2), preferred are the following compounds (2a) and (2b).

wherein, $R^{4a}$ represents a linear, branched or cyclic, saturated or unsaturated $C_{7-19}$ hydrocarbon group which may be substituted with a hydroxy group, $Z^1$ represents a methylene or methine group, a broken line represents the presence or absence of a π bond, $X^{1a}$ represents a hydrogen atom or, together with the adjacent oxygen atom, forms an oxo group, $X^{2a}$, $X^{3a}$ and $X^{4a}$ each independently represents a hydrogen atom, a hydroxy group or an acetoxy group (with the proviso that when $Z^1$ represents a methine group, one of $X^{2a}$ and $X^{3a}$ represents a hydrogen atom and the other does not exist, and when —O—$X^{1a}$ represents an oxo group, $X^{4a}$ does not exist), $R^{5a}$ represents a hydroxymethyl group or an acetoxymethyl group, $R^{7a}$ represents a linear, branched or cyclic, saturated $C_{5-30}$ hydrocarbon group which may be substituted with hydroxy group(s), or the saturated $C_{5-30}$ hydrocarbon group in which a linear or branched, saturated or unsaturated $C_{8-22}$ fatty acid which may be substituted with hydroxy group(s) is ester-bonded at the ω-position of the hydrocarbon group, and $R^{8a}$ represents a hydrogen atom or a $C_{1-4}$ alkyl group.

Preferred are compounds in which $R^{4a}$ is a linear $C_{7-19}$, more preferably $C_{13-15}$ alkyl group, $Z^1$ is a methine group, one of $X^{2a}$ and $X^{3a}$ is a hydrogen atom, and $R^{7a}$ is a linear $C_{9-27}$ alkyl group which may be substituted with hydroxy group(s). In addition, $X^{1a}$ preferably represents a hydrogen atom or, together with an oxygen atom, forms an oxo group. More preferred examples of $R^{7a}$ include a tricosyl group, a 1-hydroxypentadecyl group, a 1-hydroxytricosyl group, a heptadecyl group, a 1-hydroxyundecyl group and a nonacosyl group having a linoleic acid ester-bonded at the ω-position of the group.

Specific examples of the natural type ceramides include Ceramide Types 1 to 7 having the below-described structures and obtained by amidation of sphingosine, dihydrosphingosine, phytosphingosine or sphingadienine (for example, FIG. 2 of J. Lipid Res., 24, 759(1983), and pig and human ceramides as described in FIG. 4 of J. Lipid Res., 35, 2069 (1994)).

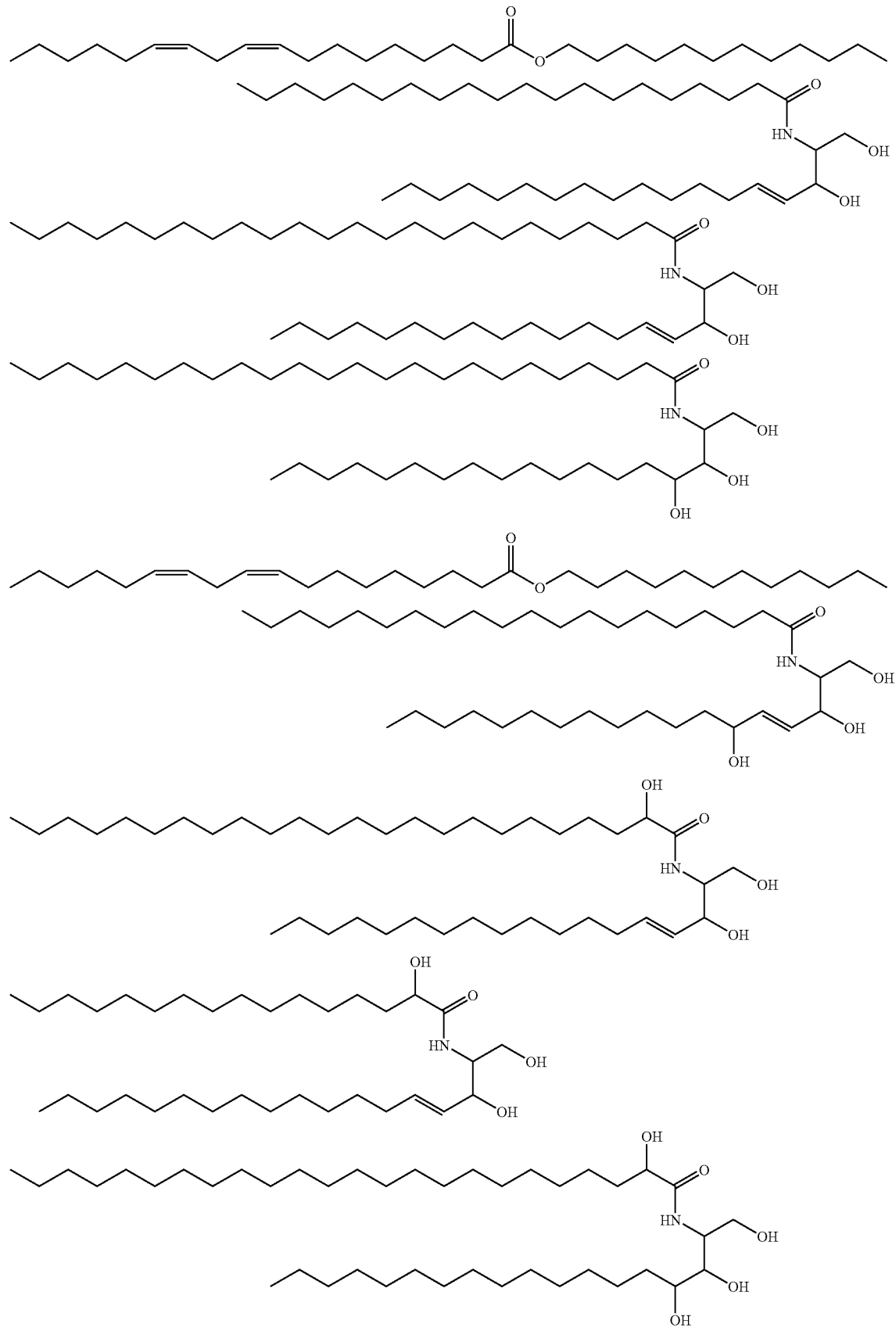

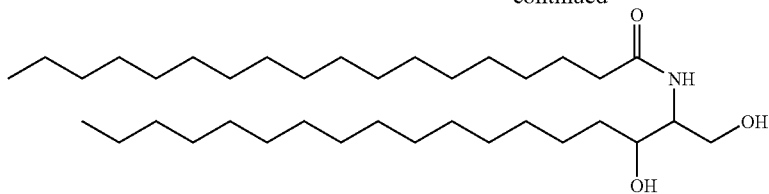

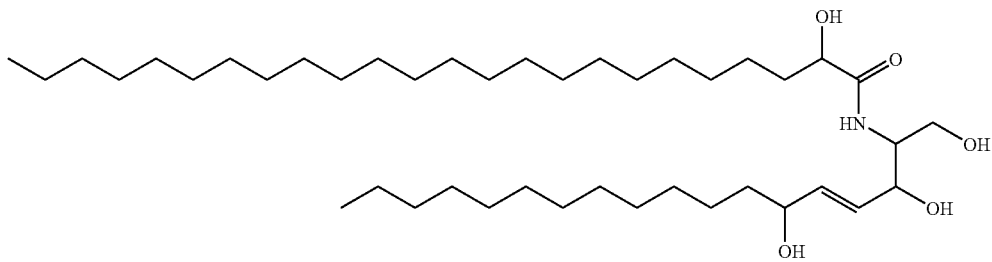

Examples also include N-alkyl derivatives (for example, N-methyl derivatives) of the above-described ceramides. They may be either a natural extract or synthesized product. Commercially available ones are also usable.

(2b) Pseudo type ceramides represented by the following formula (2b):

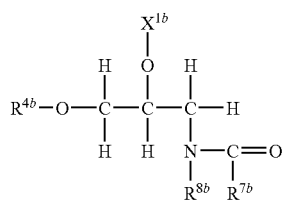

(2b)

wherein, $R^{4b}$ represents a linear, branched or cyclic, saturated or unsaturated $C_{10-22}$ hydrocarbon group which may be substituted with hydroxy group(s), $X^{1b}$ represents a hydrogen atom, an acetyl group or a glyceryl group, $R^{7b}$ represents a linear, branched or cyclic, saturated or unsaturated $C_{5-22}$ hydrocarbon group which may be substituted with hydroxy or amino group(s), or the hydrocarbon group in which a linear or branched, saturated or unsaturated $C_{8-22}$ fatty acid which may be substituted with hydroxy group(s) is ester-bonded at the ω-position of the hydrocarbon group, and $R^{8b}$ represents a hydrogen atom or an alkyl group which may be substituted with hydroxy group(s), hydroxyalkoxy group(s), alkoxy group(s) or acetoxy group(s) and has 1 to 8 carbon atoms in total.

Preferred as $R^{7b}$ are a nonyl group, a tridecyl group, a pentadecyl group, an undecyl group having linoleic acid ester-bonded at the ω-position of the group, a pentadecyl group having linoleic acid ester-bonded at the ω-position of the group, a pentadecyl group having 12-hydroxystearic acid ester-bonded at the ω-position of the group, and an undecyl group having methyl-branched isostearic acid amide-bonded at the ω-position of the group. As the hydroxyalkoxy or alkoxy groups for $R^{8b}$, preferred are those having 1 to 8 carbon atoms.

As the pseudo type ceramides (2b), those having as $R^{4b}$ a hexadecyl group, as $X^{1b}$ a hydrogen atom, as $R^{7b}$ a pentadecyl group, and as $R^{8b}$ a hydroxyethyl group; those having as $R^{4b}$ a hexadecyl group, as $X^{1b}$ a hydrogen atom, as $R^{7b}$ a nonyl group, and as $R^{8b}$ a hydroxyethyl group; or those having as $R^{4b}$ a hexadecyl group, as $X^{1b}$ a glyceryl group, as $R^{7b}$ a tridecyl group, and as $R^{8b}$ a 3-methoxypropyl group are preferred, with those having as $R^{4b}$ a hexadecyl group, as $X^{1b}$ a hydrogen atom, as $R^{7b}$ a pentadecyl group, and as $R^{8b}$ a hydroxyethyl group being more preferred. Specific preferred examples include those represented by the following formulas:

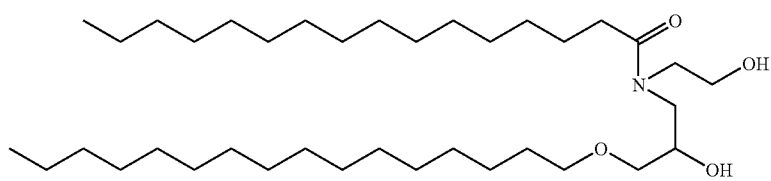

-continued

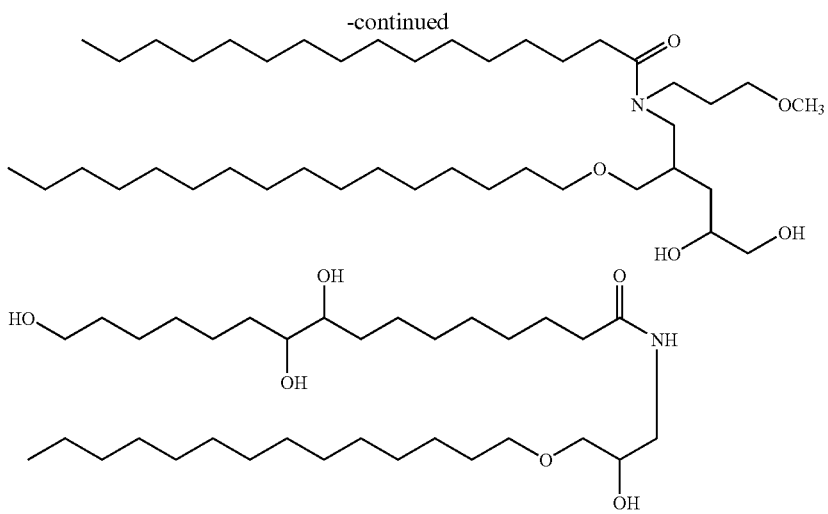

(3) Diamide compounds represented by the following formula (3):

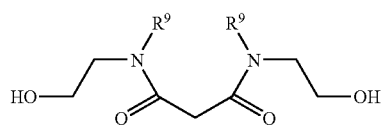

wherein, $R^9$ represents a $C_{10-18}$ alkyl group which may be substituted with hydroxy group(s).

Specific examples of compound (3) include the compound represented by the following formula:

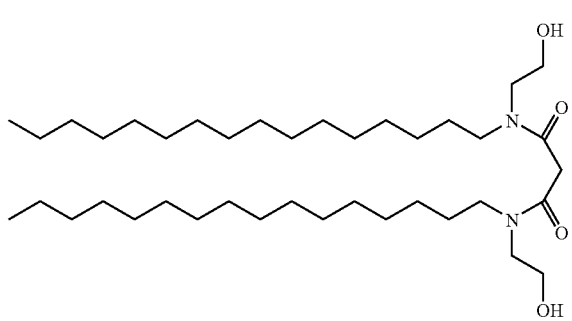

(4) Amide compounds represented by the following formula (4):

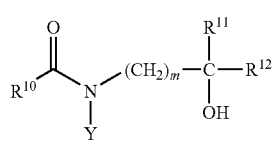

wherein, $R^{10}$ represents a linear or branched, saturated or unsaturated $C_{9-31}$ alkyl group which may be substituted with hydroxy group(s), or a 2-dodecen-1-yl succinic acid residue, m stands for an integer of from 1 to 3, $R^{11}$ and $R^{12}$ each represents a hydrogen atom or a $C_{1-4}$ alkyl or hydroxyalkyl group, Y represents a linear or branched, saturated or unsaturated $C_{10-32}$ alkyl group which may be substituted with hydroxy group(s), or a substituent represented by the following formula:

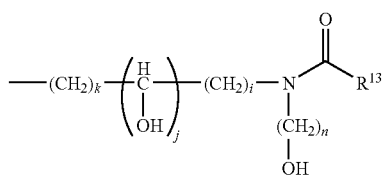

in which, k, i and n each stands for an integer of from 1 to 3, j stands for 0 or 1, and $R^{13}$ represents a linear or branched, saturated or unsaturated $C_{9-31}$ alkyl group which may be substituted with hydroxy group(s).

Specific examples of Compound (4) include a compound represented by the following formula:

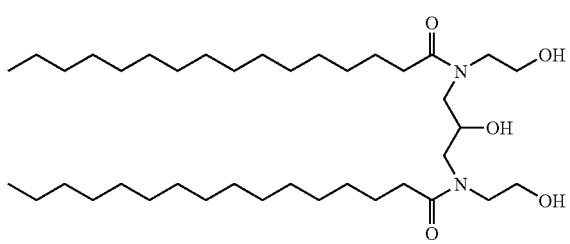

Of the above-described amphipathic amide lipids, those represented by formula (1) or (2) are preferred, and those represented by formula (1) are more preferred.

As Component (A), two or more of these amphipathic amide lipids may be used in combination. Its (their) content in the hair cleansing composition of the present invention is preferably by weight of the composition from 0.001 to 20 wt. %, more preferably from 0.1 to 15 wt. %, even more preferably from 0.2 to 3 wt. % in view of imparting suppleness to hair and preventing split ends or breakage of hair.

The anionic surfactants as Component (B) include alkyl (or alkenyl) sulfates, polyoxyalkylene alkyl (or alkenyl) ether sulfates, alkane sulfonates, olefin sulfonates, alkylbenzene sulfonates, alkyl (or alkenyl) sulfosuccinates, dialkyl (or dialkenyl) sulfosuccinates, polyoxyalkylene alkyl (or alkenyl) sulfosuccinates, alkyl (or alkenyl) ether carboxylates, polyoxyalkylene alkyl (or alkenyl) ether carboxylates, polyoxyalkylene alkyl (or alkenyl) ether phosphates, fatty acid salts, N-acyl glutamates, N-acyl taurates, and N-acylmethyltaurine. Of these, polyoxyethylene alkyl ether sulfates, polyoxyethylene alkenyl ether sulfates and alkyl sulfates are preferred, with those represented by the below-described formula (B1) or (B2) being more preferred.

$$R^{14}O(CH_2CH_2O)_aSO_3M \quad (B1)$$

$$R^{15}OSO_3M \quad (B2)$$

wherein, $R^{14}$ represents a $C_{10-18}$ alkyl or alkenyl group, $R^{15}$ represents a $C_{10-18}$ alkyl group, M represents an alkali metal, alkaline earth metal, ammonium, alkanolamine or basic amino acid, and a is a weight average number of from 1 to 5.

As Component (B), two or more of the above-described compounds may be used in combination. Its (their) content in the hair cleansing composition of the present invention is by weight of the composition, preferably from 1 to 50 wt. %, more preferably from 8 to 30 wt. %, even more preferably from 10 to 22 wt. % from the viewpoint of foaming properties, liquid properties during use and cleansing ability.

Examples of the silicone as Component (C) include dimethylpolysiloxanes, polyether-modified silicones, amino-modified silicones, carboxyl-modified silicones, methylphenylpolysiloxanes, fatty acid-modified silicones, aliphatic alcohol-modified silicones, epoxy-modified silicones, fluorine-modified silicones, cyclic silicones, and alkyl-modified silicones. Of these, dimethylpolysiloxanes, polyether-modified silicones, and amino-modified silicones are preferred. Use of the dimethylpolysiloxanes, polyether-modified silicones and amino-modified silicones can impart hair with good lubricity, smoothness and moist feeling, respectively. As the dimethylpolysiloxanes, those having a viscosity of from 5 mm²/s to 10 million mm²/s can be used depending on the intended feeling to the touch, wherein those having a viscosity of 10 million mm²/s are often supplied in the form of an emulsion. Of these, those having a viscosity falling within a range of from 5000 mm²/s to 10 million mm²/s are preferred, and those having a viscosity in the range of from 50000 mm²/s to 10 million mm²/s are more preferred. The term "polyether-modified silicones" is a generic name of polyoxyethylene-methylpolysiloxane copolymers and poly(oxyethylene-oxypropylene)methylpolysiloxane copolymers and those having various HLBs are known. Examples of the commercially available products thereof include "Silicone KF351A", "Silicone KF353A", "Silicone KF6008", "Silicone KF6016", "Silicone KF6011", and "Silicone KF6012" (each, trade name; product of Shin-etsu Chemical Co., Ltd.), "DC8500" (trade name; product of Dow Corning Corporation), and "SH3771C, "SH3773C", and "SH3775C" (each, trade name; product of Dow Corning Toray Silicone Co., Ltd.). As the polyether-modified silicones, those having an HLB of from 4 to 18, especially from 7 to 11, as measured by the Griffin method, are preferred. As the amino-modified silicones, amodimethicone oil or an emulsion thereof is usable. Their commercially available products include amodimethicone emulsion "SM8704C" (trade name; product of Dow Corning Toray Silicone Co., Ltd.) and "XF-42B1989" (trade name; product of GE Toshiba Silicones Co., Ltd.).

As Component (C), two or more of the above-described silicones may be used in combination and its (or their) content in the hair cleansing composition of the present invention is by weight of the composition, preferably from 0.005 to 5 wt. %, more preferably from 0.01 to 4 wt. %, even more preferably from 0.1 to 2 wt. %.

The silicones as Component (C) are each preferably dispersed in the hair cleansing composition and their average particle size is preferably from 0.001 to 200 μm. From the viewpoint of the stability of the composition, the average particle size is preferably from 0.001 to 10 μm, more preferably from 0.1 to 5 μm. From the viewpoint of improving the feeling to the touch during hair drying, the average particle size is preferably from 50 to 150 μm, more preferably from 80 to 120 μm.

From the viewpoint of compatibility of suppleness, smoothness and moist feeling of hair, the weight ratio of Component (A) to Component (C) is in a range of preferably from 1:1 to 1:50, more preferably from 1:2 to 1:20, still more preferably from 1:2 to 1:10.

For improving foaming performance, a surfactant other than Component (B), preferably a nonionic surfactant or amphoteric surfactant, may be incorporated in the hair cleansing composition of the present invention.

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, alkyl glycosides and glyceryl ethers. Of these, alkyl glycosides, polyoxyalkylene ($C_8$ to $C_{20}$) fatty acid esters, polyoxyethylene sorbitan fatty acid esters, polyoxyethylene hydrogenated castor oils and fatty acid alkanolamides are preferred. As the fatty acid alkanolamides, those having a $C_{8-18}$ acyl group are preferred, and those having a $C_{10-16}$ acyl group are more preferred. As the fatty acid alkanolamides, either monoalkanolamides or dialkanolamides may be used, with those having a $C_{2-3}$ hydroxyalkyl group being preferred. Examples thereof include oleic acid diethanolamide, palm kernel fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide and lauric acid monoethanolamide.

As the amphoteric surfactant, betaine surfactants can be used. Of these, betaine surfactants such as alkyldimethylaminoacetic acid betaines and fatty acid amidopropyl betaines are preferred, with fatty acid amidopropyl betaines being more preferred. As the fatty acid amidopropyl betaines, those having a $C_{8-18}$ acyl group are preferred, and those having a $C_{10-16}$ acyl group are more preferred, with laurylamidopropyl betaine, palm kernelamidopropyl betaine and cocamidopropyl betaine being even more preferred.

Two or more of these surfactants may be used in combination. Its (or their) content in the whole composition is preferably from 0.01 to 20 wt. %, more preferably from 0.05 to 10 wt. %, even more preferably from 0.1 to 5 wt. %.

To the hair cleansing composition of the present invention, cationic polymers ordinarily employed as a component for improving the feeling to the touch may be added further for improving the feeling upon use.

Examples of the cationic polymer include polydimethyldiallylammonium chlorides, acrylamidopropyltrimethylammonium chloride/acrylate copolymers, acrylamide/dimethyldiallylammonium chloride copolymers, methylvinylimidazolinium chloride/vinylpyrrolidone copolymers, a hydroxyethyl cellulose/diallyldimethylammonium chloride copolymers, diethylsulfates of vinylpyrrolidone/dimethylaminoethyl methacrylate copolymers, vinylpyrrolidone/dimethylaminoethylmethyl methacrylate copolymers, vinylpyrrolidone/alkylaminoacrylate/vinylcaprolactam copolymers, vinylpyrrolidone/dimethylaminopropylmethacrylamide copolymers, chlorinated O-[2-hydroxy-3-(trimethylammonio)propyl]hydroxy cellulose, and guar hydroxypropyltrimonium chloride. Of these, chlorinated O-[2-hydroxy-3-(trimethylammonio)propyl]hydroxy cellulose and guar hydroxypropyltrimonium chloride are preferred from the viewpoint of the feeling. Two or more of these cationic polymers may be used in combination. Its (or their) content in the whole composition is, as a solid content, preferably from 0.01 to 20 wt. %, more preferably from 0.05 to 10 wt. %, even more preferably from 0.1 to 5 wt. %.

The hair cleansing composition of the present invention can contain, in addition to the above-described components, oil components such as higher alcohols, lanolin derivatives, and polyethylene glycol fatty acid esters; water soluble polymers such as hydroxypropylmethyl cellulose, hydroxy cellulose, polyvinyl alcohol, and polyethylene glycol; polyhydric alcohols such as sorbitol; humectants; chelating agents such as ethylenediaminetetraacetic acid (EDTA); drugs such as vitamin preparations; amino acids and derivatives thereof; fine particles of a polymer such as polyethylene, polystyrene, poly(methyl methacrylate), nylon or silicone, and hydrophobic products thereof; extracts derived from animals or plants; ultraviolet absorbers; pearling agents; antiseptics; bactericides; pH regulators; colorants; and fragrances, according to the intended use.

From the viewpoint of compatibility of suppleness, smoothness and moist feeling of hair, the hair cleansing composition of the present invention has a pH preferably not less than 4.6 and less than 7, more preferably not less than 5 and less than 6 when applied to hair (i.e. when diluted 20 times by weight with water at 25° C.).

The hair cleansing composition of the present invention can be provided in any form such as liquid, powder, gel or granule as needed. A liquid composition using water or a lower alcohol as a solvent is preferred, with an aqueous solution being more preferred.

EXAMPLES

The following examples further describe and demonstrate embodiments of the present invention. The examples are given solely for the purpose of illustration and are not to be construed as limitations of the present invention. In the below-described Examples and Comparative Examples, the following amphipathic amide lipids were employed.

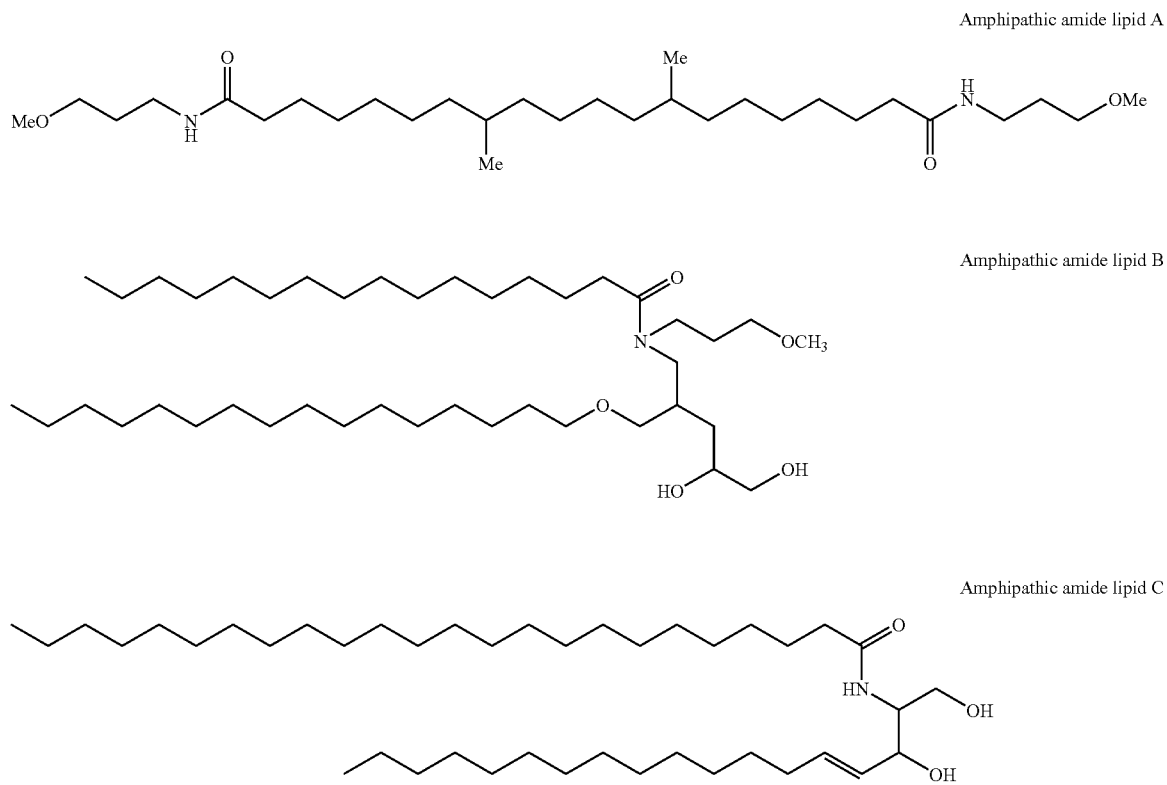

Amphipathic amide lipid A

Amphipathic amide lipid B

Amphipathic amide lipid C

Ceramide 2

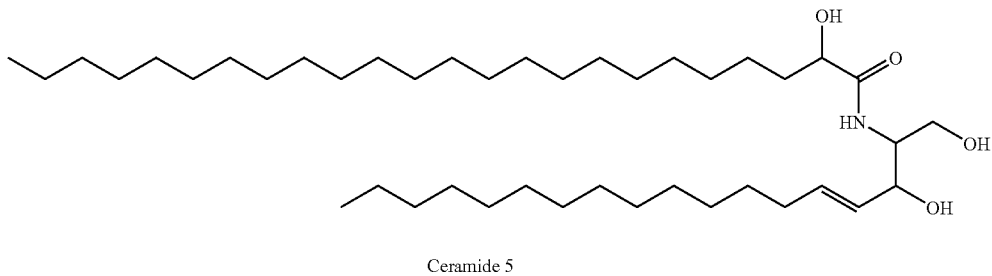

Ceramide 5

The pH in the below description is a value of the composition diluted with water to 20 times the weight of the composition when measured at 25° C.

Examples 1 to 3, and Comparative Examples 1 to 3

Shampoos as shown in Table 1 were prepared in the conventional manner and they were evaluated.

(1) Smoothness and Moist Feeling

A bundle of 20 g (15 cm in length) of the hair of a healthy Japanese female was made and 1 g of the shampoo in Table 1 was applied to the hair bundle. After one minute of foaming, the hair was rinsed with running water for 30 seconds, followed by towel drying and then drying with a hair dryer. The "smoothness" and "moist feeling" of the dried hair were organoleptically evaluated in accordance with the following criteria:

Smoothness:

A: The hair is imparted with natural and sufficient smoothness.

B: The hair is imparted with smoothness.

C: It is difficult to evaluate whether the hair is imparted with smoothness or not.

D: Friction appears among individual hairs.

Moist Feeling:

A: The hair became very moist to the touch.

B: The hair became moist to the touch.

C: It is difficult to evaluate whether the hair became moist to the touch or not.

D: The hair does not become moist to the touch.

(2) Effects of Preventing Split Ends and Breakage of Hair

About 20 g (about 15 to 20 cm long) of the hair of a Japanese female, which had not been subjected to any chemical treatment such as permanent waving and hair dyeing, was treated with "LAVENUS Pure Color Neo Red Nuance" (trade name; product of Kao Corporation) (bath ratio 1:1) at room temperature for 20 minutes. After the treatment, cleansing with a plain shampoo and a plain rinse was conducted. The plain shampoo and plain rinse used here have the following compositions, respectively:

| | (wt. %) |
|---|---|
| Plain Shampoo | |
| A 25 wt.% solution of sodium polyoxyethylene (2.5) lauryl ether sulfate | 62.0 |
| Lauric acid diethanolamide | 2.28 |
| Disodium edetate | 0.10 |
| Sodium benzoate | 0.50 |
| Oxybenzone | 0.03 |
| Phosphoric acid (75 wt.%) | 0.10 |
| Dibutyihydroxytoluene | 0.01 |
| Sodium chloride | 0.80 |
| Red No. 106 | 0.00012 |
| Fragrance | 0.26 |
| Purified water | Balance |
| Plain Rinse | |
| Stearyltrimethylammonium chloride (28 wt. %) | 2.7 |
| Distearyldimethylammonium chloride | 3.6 |
| Cetanol | 2.0 |
| Propylene glycol | 5.0 |
| Methyl p-hydroxybenzoate | 0.1 |
| Deionized water | Balance |

The hair bundle subjected to the above-described cleansing treatment was shampooed once with the shampoo of Table 1 and after drying, was brushed predetermined times (100 times/min×90 minutes) at 25 to 27° C. and 21 to 25% RH. Generation of split ends after brushing was evaluated in accordance with the below-described criteria in comparison with that before brushing.

A: An increase in split ends or breakage of the hair is not recognized.

B: An increase in split ends or breakage of the hair is scarcely recognized.

C: A slight increase in split ends or breakage of the hair is recognized.

D: An increase in split ends or breakage of the hair is recognized.

TABLE 1

(wt.%)

|   |   | Examples | | | Comparative Examples | | |
|---|---|---|---|---|---|---|---|
|   |   | 1 | 2 | 3 | 1 | 2 | 3 |
| (A) | Amphipathic amide lipid A | 2 | 2 | — | 2 | — | — |
|   | Amphipathic amide lipid B | — | — | 2 | — | — | — |
| (B) | Sodium polyoxyethylene (2) lauryl ether sulfate | 10 | 10 | 10 | 10 | 10 | 10 |
|   | Sodium lauryl sulfate | 5 | 5 | 5 | 5 | 5 | 5 |
| (C) | Dimethylpolysiloxane emulsion *1 | 2 | 2 | — | — | — | — |
|   | Amino-modified silicone *2 | — | 0.5 | 0.5 | — | 0.5 | — |
| Other | Myristyl alcohol | 1 | 1 | 1 | 1 | 1 | 1 |
|   | Cocoylmonoethanolamide | 0.5 | 0.5 | 0.5 | 0.5 | 0.5 | 0.5 |
|   | Ethylene glycol distearate | 1 | 1 | 1 | 1 | 1 | 1 |
|   | Cationized hydroxyethyl cellulose | 0.3 | 0.3 | 0.3 | 0.3 | 0.3 | 0.3 |
|   | Cationized guar gum | 0.5 | 0.5 | 0.5 | 0.5 | 0.5 | 0.5 |
|   | PH regulator (sodium hydroxide, citric acid) | q.s. *3 | q.s. *3 | q.s. *3 | q.s. *3 | q.s. *3 | q.s. *3 |
|   | Purified water | Balance | Balance | Balance | Balance | Balance | Balance |
|   | pH | 5.5 | 5.5 | 5.5 | 5.5 | 5.5 | 5.5 |
| Evaluation | Smoothness of hair | B | A | A | C | C | C |
|   | Moist feeling of hair | A | A | A | B | B | C |
|   | Prevention of split ends or breakage | A | A | B | A | C | C |

*1 "CF-2460" (trade name; product of Dow Corning Toray Silicone, a 75 wt. % emulsion, average particle size: about 100 μm)
*2 "SM8704C" (trade name; product of Dow Corning Toray Silicone, a 40 wt. % emulsion, average particle size: about 0.5 μm)
*3 An amount to adjust the pH

Example 4

Shampoo

|   | (wt. %) |
|---|---|
| Sodium polyoxyethylene (2) lauryl ether sulfate | 10.0 |
| Sodium lauryl sulfate | 5.0 |
| Cationized guar gum | 0.1 |
| Amphipathic amide lipid A | 0.2 |
| Malic acid | 0.75 |
| Sodium chloride | 1.0 |
| Laurylamidopropyl betaine | 1.0 |
| Cocoylmonoethanolamide | 0.3 |

Dimethicone-Containing Emulsion

| | |
|---|---|
| ("CF-2460", trade name; product of Dow Corning Toray Silicone, a 75 wt. % emulsion, average particle size: about 100 μm) | 0.5 |
| Propylene carbonate | 0.5 |
| Glycerin | 1.0 |
| Sodium hydroxide | An amount to adjust the pH |
| Deionized water | balance |

The above-described shampoo (pH 6.0) can provide hair with good smoothness and moist feeling after use and prevents split ends or breakage of hair.

Example 5

Conditioning Shampoo

|   | (wt. %) |
|---|---|
| Sodium polyoxyethylene (2) lauryl ether sulfate | 8.0 |
| Sodium lauryl sulfate | 5.0 |
| Cationized guar gum | 0.5 |
| Amphipathic amide lipid A | 2.0 |
| Maleic acid | 0.75 |
| Trisodium citrate | 0.1 |
| LaurylamidOpropyl betaine | 3.0 |
| 2-Ethylhexyl monoglyceryl ether | 0.7 |

Dimethicone-Containing Emulsion

| | |
|---|---|
| ("CF-2460", trade name; product of Dow Corning Toray Silicone, a 75 wt. % emulsion, average particle size: about 100 μm) | 1.5 |

Amodimethicone-Containing Emulsion

| | |
|---|---|
| ("SM8704C", trade name; product of Dow Corning Toray Silicone, a 40 wt. % emulsion, average particle size: about 0.5 μm) | 0.1 |
| Myristyl alcohol | 1.0 |
| Ethylene glycol distearate | 3.0 |

-continued

| | |
|---|---|
| Propylene glycol (MW = 400) | 0.5 |
| Glycerin | 1.0 |
| Sodium hydroxide | An amount to adjust the pH |
| Deionized water | balance |

The above-described shampoo (pH 5.5) can provide hair with good smoothness and moist feeling after use and prevent split ends or breakage of hair.

Example 6

Conditioning Shampoo

| | (wt. %) |
|---|---|
| Sodium polyoxyethylene (2) lauryl ether sulfate | 11.0 |
| Sodium lauryl sulfate | 5.0 |
| Cationized guar gum | 0.3 |
| Amphipathic amide lipid B | 2.0 |
| Malic acid | 0.75 |
| Lactic acid | 0.1 |
| Sodium chloride | 0.2 |
| Benzyl alcohol | 0.5 |
| Cocoylmonoethanolamide | 1.0 |

Amodimethicone-Containing Emulsion

| | |
|---|---|
| ("SM8704C", trade name; product of Dow Corning Toray Silicone, a 40 wt. % emulsion, average particle size: about 0.5 μm) | 0.1 |
| Myristyl alcohol | 1.0 |
| Cetanol | 0.5 |
| Ethylene glycol distearate | 3.0 |
| Cationic hydroxyethyl cellulose | 0.3 |
| Glycerin | 1.0 |
| Sodium hydroxide | An amount to adjust the pH |
| Deionized water | balance |

The above-described shampoo (pH 5.5) can provide hair with good smoothness and moist feeling after use and prevent split ends or breakage of hair.

Example 7

Conditioning Shampoo

| | (wt. %) |
|---|---|
| Sodium polyoxyethylene (2) lauryl ether sulfate | 8.0 |
| Cationized guar gum | 0.3 |
| Amphipathic amide lipid C | 0.05 |
| Amphipathic amide lipid D | 0.1 |
| Malic acid | 0.5 |
| Lactic acid | 0.5 |
| Sodium chloride | 1.0 |
| Laurylamidopropyl betaine | 3.0 |

Dimethicone-Containing Emulsion

| | |
|---|---|
| "CF-2460", trade name; product of Dow Corning Toray Silicone, a 75 wt. % emulsion, average particle size: about 100 μm) | 1.5 |

Amodimethicone-Containing Emulsion

| | |
|---|---|
| ("SM8704C", trade name; product of Dow Corning Toray Silicone, a 40 wt. % emulsion, average particle size: about 0.5 μm) | 0.1 |
| Myristyl alcohol | 1.0 |
| Cetanol | 0.5 |
| Behenyltrimonium chloride | 0.5 |
| Ethylene glycol distearate | 2.0 |
| Benzyloxyethanol | 0.5 |
| Sodium hydroxide | An amount to adjust the pH |
| Deionized water | balance |

The above-described shampoo (pH 5.5) can provide hair with good smoothness and moist feeling after use and prevent split ends or hair breakage.

What is claimed is:

1. A hair cleansing composition comprising the following components (A) to (C):

(A): an amphipathic amide lipid represented by the formula (1):

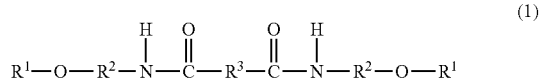

wherein, $R^1$ represents a linear or branched $C_{1-12}$ hydrocarbon group which may be substituted with hydroxy group(s) and/or alkoxy group(s), $R^2$ represents a linear or branched divalent $C_{1-5}$ hydrocarbon group, and $R^3$ represents a linear or branched divalent $C_{1-22}$ hydrocarbon group, (B): an anionic surfactant, and (C): from 0.005 to 5 wt. % of a silicone, wherein a weight ratio of Component (A) to Compound (C) is from 1:1 to 1:50.

2. The hair cleansing composition of claim 1, wherein the silicone is selected from the group consisting of dimethylpolysiloxane, polyether-modified silicones, amino-modified silicones, and mixtures thereof.

3. The hair cleansing composition of claim 1, wherein the anionic surfactant is selected from the group consisting of alkyl (or alkenyl) sulfates, polyoxyalkylene alkyl (or alkenyl) ether sulfates, alkane sulfonates, olefin sulfonates, alkylbenzene sulfonates, alkyl (or alkenyl) sulfosuccinates, dialkyl (or dialkenyl) sulfosuccinates, polyoxyalkylene alkyl (or alkenyl) sulfosuccinates, alkyl (or alkenyl) ether carboxylates, polyoxyalkylene alkyl (or alkenyl) ether carboxylates, polyoxyalkylene alkyl (or alkenyl) ether phosphates, fatty acid salts, N-acyl glutamates, N-acyl taurates, N-acylmethyltaurine, and mixtures thereof.

4. The hair cleansing composition of claim 1, comprising from 1 to 50 wt. % of Component (B).

5. The hair cleansing composition of claim 1, further comprising a surfactant selected from the group consisting of a nonionic surfactant, amphoteric surfactant, and mixtures thereof.

6. The hair cleansing composition of claim 1, wherein the weight ratio of Component (A) to Compound (C) is from 1:2 to 1:20.

7. The hair cleansing composition of claim 1, wherein the weight ratio of Component (A) to Compound (C) is from 1:2 to 1:10.

8. The hair cleansing composition of claim 1, wherein the silicone has a viscosity from 5 $mm^2/s$ to 10 million $mm^2/s$.

9. The hair cleansing composition of claim 1, wherein the silicone is dispersed in the cleansing composition and an average particles size of the silicone is from 0.001 to 200 μm.

10. The hair cleansing composition of claim 4, comprising from 10 to 22 wt. % of Component (B).

11. The hair cleansing composition of claim 1, comprising from 0.1 to 2 wt. % of the silicone.

* * * * *

UNITED STATES PATENT AND TRADEMARK OFFICE
CERTIFICATE OF CORRECTION

| | | |
|---|---|---|
| PATENT NO. | : 7,612,141 B2 | Page 1 of 1 |
| APPLICATION NO. | : 11/245071 | |
| DATED | : November 3, 2009 | |
| INVENTOR(S) | : Sakai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 737 days.

Signed and Sealed this

Nineteenth Day of October, 2010

David J. Kappos
*Director of the United States Patent and Trademark Office*